(12) United States Patent
Strong et al.

(10) Patent No.: US 9,958,067 B2
(45) Date of Patent: May 1, 2018

(54) LIQUID DISPENSING SYRINGE

(75) Inventors: Warren N. Strong, Hope, RI (US); Michael A. Vidal, North Attleborough, MA (US); Terrence Woldorf, Westport, MA (US)

(73) Assignee: Nordson Corporation, Westlake, OH (US)

( * ) Notice: Subject to any disclaimer, the term of this patent is extended or adjusted under 35 U.S.C. 154(b) by 2268 days.

(21) Appl. No.: 11/761,678

(22) Filed: Jun. 12, 2007

(65) Prior Publication Data

US 2007/0287965 A1 Dec. 13, 2007

Related U.S. Application Data

(60) Provisional application No. 60/813,424, filed on Jun. 13, 2006.

(51) Int. Cl.
*A61M 5/20* (2006.01)
*F16J 1/00* (2006.01)
(Continued)

(52) U.S. Cl.
CPC ......... *F16J 1/003* (2013.01); *B05C 17/00576* (2013.01); *A61M 5/2053* (2013.01);
(Continued)

(58) Field of Classification Search
CPC ............ A61M 5/31511; A61M 5/3153; A61M 5/31515; A61M 2005/3156; A61M 2005/3152; A61M 2005/31523; A61M 2005/3101; A61M 5/3135; A61M 2005/3131; A61M 2005/3139; A61M 5/1452–5/1458; B05C 17/00573;
(Continued)

(56) References Cited

U.S. PATENT DOCUMENTS 1,948,982 A * 2/1934 Cutter .......................... 604/222
2,830,586 A 4/1958 Dann et al.
(Continued)

FOREIGN PATENT DOCUMENTS

GB 2020254 A 11/1979
JP 5-208157 A 8/1993
(Continued)

OTHER PUBLICATIONS

European Patent Office, Invitation to Pay Additional Fees and Partial Search Report in PCT Application Serial No. PCT/US2007/070971, dated Nov. 29, 2007.
(Continued)

*Primary Examiner* — Aarti B Berdichevsky
*Assistant Examiner* — Laura Schell
(74) *Attorney, Agent, or Firm* — Baker & Hostetler LLP

(57) ABSTRACT

A syringe for dispensing liquid materials to a substrate. In one embodiment, the syringe includes a barrel having a first end, a second end, and an interior reservoir. A piston is slidably disposed within the reservoir and is movable to increase or decrease a volume of the interior reservoir near the first end of the barrel. A first end of the piston has a hemispherically-shaped surface profile, with an elongated apex extending therefrom, to dispense liquid from the first end of the barrel when the piston is moved in a direction toward the first end.

15 Claims, 6 Drawing Sheets

(51) Int. Cl.
  *B05C 17/005* (2006.01)
  *A61M 5/315* (2006.01)
  *A61M 5/34* (2006.01)
  *A61M 5/31* (2006.01)

(52) U.S. Cl.
  CPC ......... *A61M 5/31511* (2013.01); *A61M 5/347* (2013.01); *A61M 2005/3104* (2013.01); *A61M 2005/3123* (2013.01); *A61M 2005/31516* (2013.01)

(58) Field of Classification Search
  CPC ............ B05C 17/015; B05C 17/00576; B65D 83/0005; F16J 1/003
  USPC ... 604/152, 154, 218, 222, 230, 256, 38, 57, 604/68, 110, 187, 181, 220, 221, 225, 604/228, 229, 231; 401/176, 179, 182
  See application file for complete search history.

(56) References Cited

U.S. PATENT DOCUMENTS

| | | | |
|---|---|---|---|
| 2,952,255 A | 9/1960 | Hein, Jr. | |
| 3,149,717 A | 9/1964 | Castelli | |
| 3,237,815 A | 3/1966 | Ogle | |
| 3,331,538 A * | 7/1967 | Higgins | 222/387 |
| 3,827,607 A * | 8/1974 | Schultz | B65D 83/64 |
| | | | 222/389 |
| 4,067,332 A | 1/1978 | O'Leary | |
| 4,231,494 A * | 11/1980 | Greenwood | 222/325 |
| 4,266,557 A * | 5/1981 | Merry | 600/576 |
| D262,739 S | 1/1982 | Nitshke | |
| 4,708,270 A | 11/1987 | Ruesch | |
| D294,640 S | 3/1988 | Wichen et al. | |
| D302,206 S | 7/1989 | McAlister et al. | |
| D306,069 S | 2/1990 | Kelly et al. | |
| 4,940,460 A * | 7/1990 | Casey | A61M 5/30 |
| | | | 604/131 |
| D321,759 S | 11/1991 | Buswell et al. | |
| 5,086,780 A * | 2/1992 | Schmitt | A61B 5/15003 |
| | | | 600/573 |
| 5,098,416 A * | 3/1992 | Imonti | 604/319 |
| D338,957 S | 8/1993 | De Faire et al. | |
| 5,238,003 A * | 8/1993 | Baidwan | A61B 5/15003 |
| | | | 600/578 |
| 5,273,187 A | 12/1993 | Suzuki | |
| D345,016 S | 3/1994 | Stamler | |
| 5,322,440 A * | 6/1994 | Steele | 433/90 |
| 5,324,265 A * | 6/1994 | Murray | A61M 5/3234 |
| | | | 604/110 |
| 5,338,307 A * | 8/1994 | Stephens et al. | 604/167.01 |
| 5,496,285 A * | 3/1996 | Schumacher et al. | 604/218 |
| 5,509,903 A | 4/1996 | Grendahl et al. | |
| 5,531,710 A * | 7/1996 | Dang et al. | 604/238 |
| D375,358 S | 11/1996 | Clark | |
| D383,538 S | 9/1997 | Erskine et al. | |
| D385,628 S | 10/1997 | Echevarria | |
| 5,752,936 A * | 5/1998 | Chen | A61B 5/15003 |
| | | | 600/576 |
| 5,795,337 A * | 8/1998 | Grimard | A61M 5/31511 |
| | | | 604/222 |
| D401,324 S | 11/1998 | Hjertman et al. | |
| 5,833,628 A | 11/1998 | Yuan et al. | |
| D405,232 S | 2/1999 | Stevens et al. | |
| 5,887,764 A * | 3/1999 | Ennis, III | B05C 17/015 |
| | | | 222/153.01 |
| D417,275 S | 11/1999 | Conforti | |
| D429,812 S | 8/2000 | Hjertman et al. | |
| D431,864 S | 10/2000 | Jansen | |
| D447,797 S | 9/2001 | Odell et al. | |
| D447,799 S | 9/2001 | Jun | |
| 6,296,625 B1 * | 10/2001 | Vetter et al. | 604/227 |
| D465,024 S | 10/2002 | Henderson et al. | |
| D486,225 S | 2/2004 | Gay, III | |
| D495,050 S | 8/2004 | Guala | |
| 6,942,638 B1 * | 9/2005 | Quinn | A61M 5/30 |
| | | | 604/222 |
| 6,984,222 B1 * | 1/2006 | Hitchins et al. | 604/218 |
| RE39,107 E * | 5/2006 | Shaw | A61B 5/15003 |
| | | | 600/576 |
| 7,070,581 B2 * | 7/2006 | Manera et al. | 604/218 |
| D543,278 S | 5/2007 | Numata et al. | |
| 7,361,162 B2 * | 4/2008 | Koller et al. | 604/227 |
| 7,775,990 B2 | 8/2010 | DeHart | |
| 8,454,708 B2 | 6/2013 | Kutsko et al. | |
| D692,143 S | 10/2013 | shahidi bonjar | |
| 2001/0021823 A1 * | 9/2001 | Nemoto | 604/154 |
| 2002/0043539 A1 * | 4/2002 | Pagel | B05C 5/0225 |
| | | | 222/207 |
| 2003/0015557 A1 * | 1/2003 | D'Alessio | A61B 17/00491 |
| | | | 222/566 |
| 2003/0168480 A1 * | 9/2003 | Kim | A61M 5/1452 |
| | | | 222/399 |
| 2004/0039341 A1 * | 2/2004 | Ranalletta | 604/199 |
| 2004/0122367 A1 * | 6/2004 | Sculati | A61F 9/0017 |
| | | | 604/140 |
| 2004/0260248 A1 * | 12/2004 | Koller et al. | 604/220 |
| 2005/0029306 A1 | 2/2005 | Brennan | |
| 2005/0209562 A1 * | 9/2005 | Kim | A61M 5/14526 |
| | | | 604/141 |
| 2006/0069356 A1 * | 3/2006 | Witowski | 604/222 |
| 2006/0089594 A1 * | 4/2006 | Landau | A61M 5/2033 |
| | | | 604/68 |
| 2007/0000951 A1 | 1/2007 | Springhom | |

FOREIGN PATENT DOCUMENTS

| | | |
|---|---|---|
| JP | 7204557 A | 8/1995 |
| JP | 8105197 A | 4/1996 |
| JP | 8266624 A | 10/1996 |
| JP | 10118556 A | 5/1998 |

OTHER PUBLICATIONS

European Patent Office; Extended Search Report in European Patent Application EP 10 15 5573 dated Jul. 23, 2010; 5 pages.

European Patent Office, International Search Report and Written Opinion in PCT Application Serial No. PCT/US2007/070971, dated Nov. 6, 2007.

Japanese Patent Office; Office Action in Japanese Patent Application No. 2009-515601 dated Nov. 6, 2012; 7 pages.

Korean Patent Office, Notice of Preliminary Rejection in JP Application No. 10-2008-7029779, dated Jan. 27, 2014.

* cited by examiner

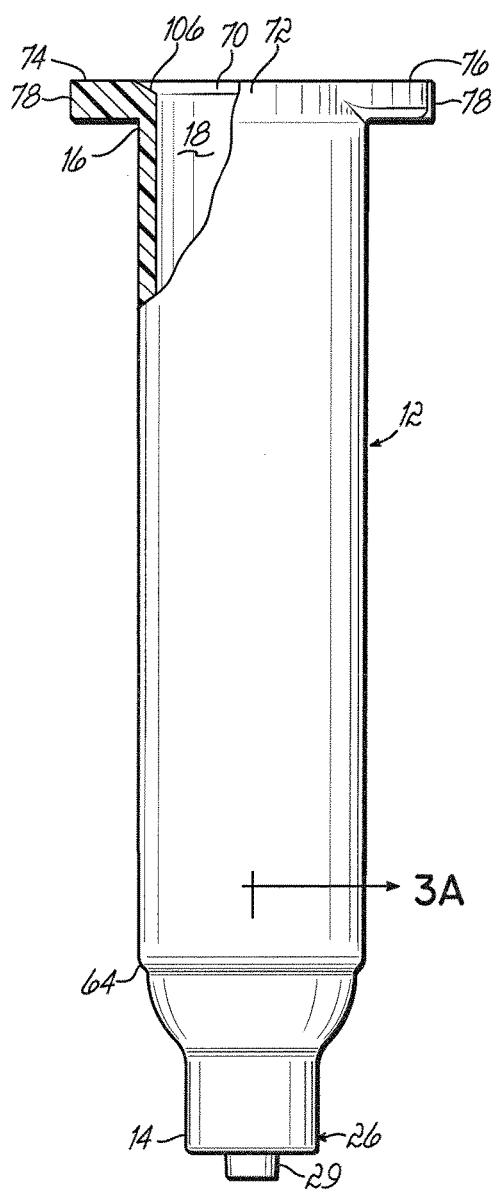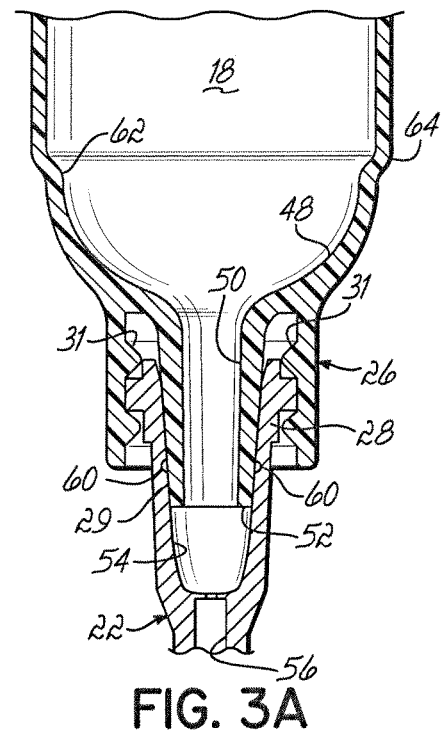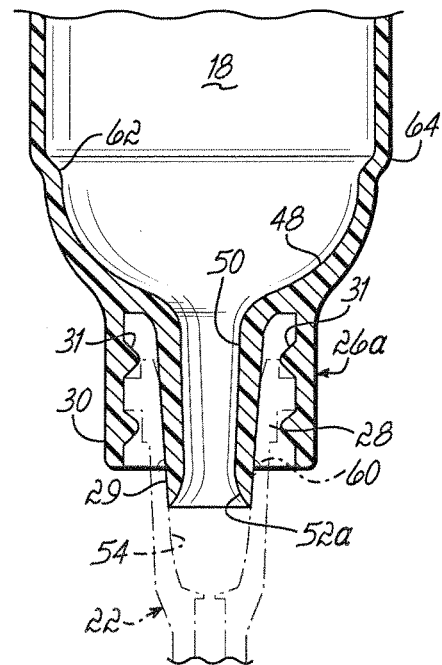

US 9,958,067 B2

1

LIQUID DISPENSING SYRINGE

The present application claims the filing benefit of U.S. Provisional Patent Application No. 60/813,424, filed Jun. 13, 2006, which is incorporated by reference herein in its entirety.

TECHNICAL FIELD

This invention relates generally to the field of dispensing liquid materials, and more particularly to a syringe for dispensing liquid materials.

BACKGROUND

Various types of dispensers are used in many industries for placing liquids, such as adhesives, conformal coating materials, solder paste, solder flux, and other similar materials, onto substrates during an assembly process. One type of liquid dispenser is a syringe-type dispenser having a dispenser body defining a barrel reservoir for holding a supply of liquid material to be dispensed. A dispensing tip is coupled to the syringe at one end, and is in fluid communication with the reservoir. A piston disposed in the reservoir is movable therein to pressurize the liquid in the reservoir and thereby dispense a small amount of liquid from the dispensing tip and onto a substrate.

Many industrial applications require that the liquid be dispensed in very precise volumes and at precise locations. To this end, liquid dispensers include actuators for moving the piston within the reservoir in a controllable and predictable manner. For instance, pneumatic actuators are known in the art and use compressed air applied to the piston to move the piston and dispense liquid from the dispenser. Those skilled in the art will recognize that other types of actuators, such as linear actuators, may be used to control movement of the piston within the reservoir. In other applications where precise dispensing is not required, the piston may be moved through manual processes.

SUMMARY

According to one aspect, a dispensing syringe includes a barrel having first and second ends, and an interior reservoir. A piston is slidably disposed within the reservoir and is movable within the reservoir between first and second positions to increase or decrease a volume at the first end of the barrel. The piston has first and second ends, and the first end has a generally hemispherical shaped surface profile with an elongated apex extending along a central axis of the piston. The surface profile facilitates dispensing fluid from the first end of the barrel when the piston is moved in a direction toward the first end. The dispensing syringe reduces or eliminates air entrapment and minimizes the volume of material left in the syringe after the piston has been fully engaged with the first end of the barrel.

In another aspect, the piston may include a circumferentially-extending wiper seal located between the first and second ends of the piston. The piston may further include one or more fluid passages defined on the hemispherically-shaped surface. The fluid passages extend between the first and second ends of the piston and help to reduce the accumulation of air beneath the first wiper when the interior reservoir is filled from the first end of the barrel. The piston may be configured to permit gas to pass from the first volume, while retaining liquid within the first volume. In one embodiment, at least a portion of the piston is textured to facilitate passing gas from the first volume, while retaining the liquid.

In another aspect, the syringe barrel includes a radially inwardly extending ledge within the interior reservoir. The ledge engages the wiper seal when the piston is moved toward the first end of the barrel to engage the piston with the first end. Engagement between the wiper seal and the ledge squeezes liquid material from beneath the wiper, thereby minimizing liquid material remaining in the reservoir when the piston is moved to the first end of the barrel.

In another aspect, an adapter for coupling a dispensing syringe to a source of pressurized air includes a first end for coupling to a syringe barrel and a second end for coupling to the source of pressurized air. First and second hubs on the first end of the adapter engage ears on the barrel to secure the adapter to the barrel. The ears of the barrel may have radial extents that are small compared to the circumferential lengths of the ears, so that deflection of the ears is reduced or eliminated during use of the dispensing syringe. The adapter may further include a seal extending from the first end of the adapter for engaging the open end of the barrel when the first and second hubs engage the ears on the barrel.

In yet another aspect, an end cap may be used with the syringe barrel when the adapter is not used to couple the syringe barrel to a source of pressurized air. The end cap includes an annular brim with first and second oppositely disposed engagement tabs. The end cap has a flexible central portion located radially inward of the brim. The flexible central portion is deformable to facilitate snap-fit installation of the engagement tabs over the ears of the barrel.

In another aspect, a tip cap may be secured to a male luer connector at the first end of the syringe barrel. The tip cap includes an end wall with a skirt and an annular boot extending axially outward from the end wall. The boot is positioned concentrically within the skirt to define a space for frictionally gripping the male luer connector therein. The tip cap further includes at least one circumferential rib on the boot for engaging corresponding threads on the male luer connector of the syringe barrel.

These and other features, objects and advantages will become more readily apparent to those skilled in the art in view of the following detailed description, taken in conjunction with the accompanying drawings.

BRIEF DESCRIPTION OF THE DRAWINGS

The accompanying drawings, which are incorporated in and constitute a part of this specification, illustrate exemplary embodiments and, together with the general description given above, and the detailed description given below, serve to explain principles of the invention.

FIG. 3 is a side elevation view of the barrel of the dispensing syringe of FIG. 1.

FIG. 3A is an enlarged cross-sectional view of the syringe barrel of FIG. 3, taken along line 3A-3A.

FIG. 3B is an enlarged cross-sectional view of an alternative embodiment of the syringe barrel of FIG. 3.

DETAILED DESCRIPTION

Figure 1:
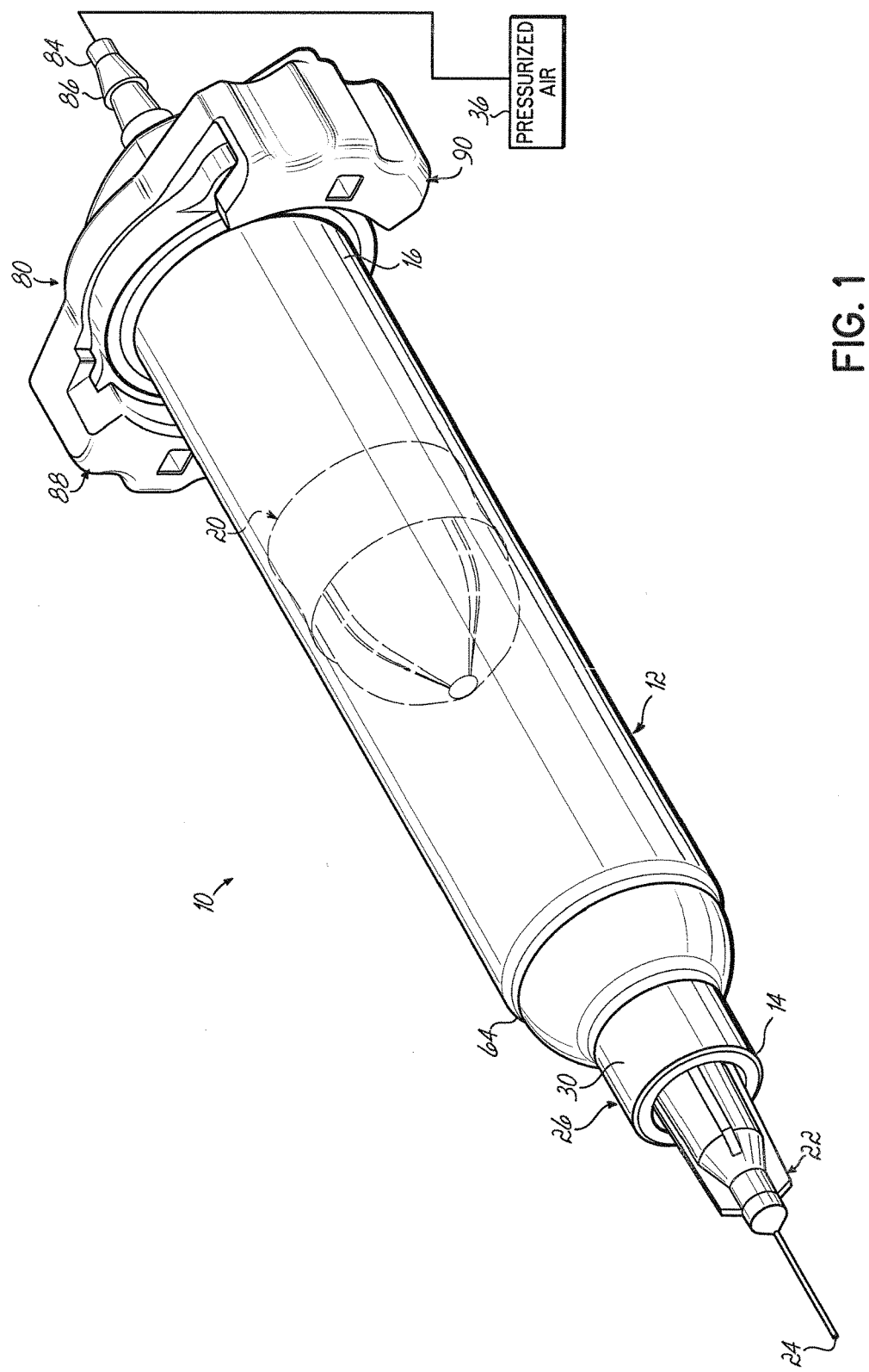
FIG. 1 is a perspective view of an exemplary dispensing syringe.

FIGS. 1, 2, 3, 3A, and 3B illustrate an exemplary liquid dispensing syringe 10. The syringe 10 comprises an elongate tubular body such as a generally elongate syringe barrel 12 having a first end 14 for dispensing liquid material therefrom, and a second end 16 opposite the first end 14. The barrel 12 defines an interior reservoir 18 (FIG. 3) for containing the liquid material to be dispensed from the first end 14. A piston 20 is slidably disposed within the interior reservoir 18 and is slidably movable therein between the first and second ends 14, 16 to thereby dispense liquid material from the first end 14 as the piston 20 moves in a direction toward the first end 14. A dispensing tip 22 is removably coupled to the first end 14 of the barrel 12 for communication with the interior reservoir 18 such that liquid material may be dispensed from an outlet 24 of the dispensing tip 22.

In the embodiment shown, the first end 14 of the barrel 12 includes a male luer connector 26 adapted to receive a corresponding female luer 28 provided on the dispensing tip 22, whereby the dispensing tip 22 may be coupled to the first end 14 of the barrel 12, as depicted in FIGS. 3, 3A, and 3B. Male luer connector 26 includes a male connecting tip 29 and a collar 30 with internal threads 31 for securing the dispensing tip 22 thereto. The second end 16 of the barrel 12 includes a comparatively large diameter opening 70 and has radially outwardly extending flanges or "ears" 74, 76 for securing an end cap 110 or an adapter 80 that facilitates coupling the second end 16 of the barrel 12 to an actuator such as a source of pressurized air 36 (FIG. 1).

Figure 2:
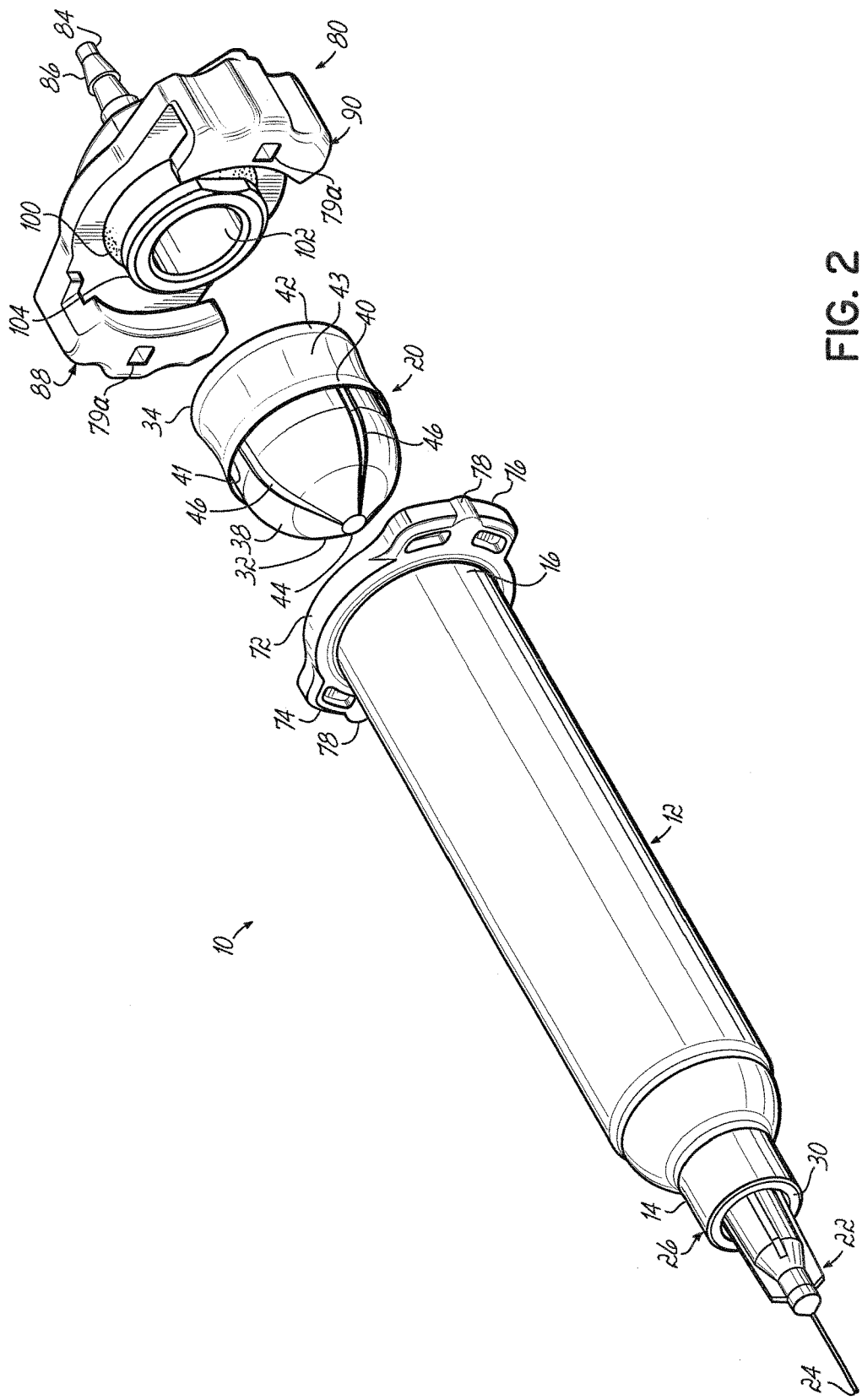
FIG. 2 is an exploded perspective view of the dispensing syringe of FIG. 1.
Figure 7:
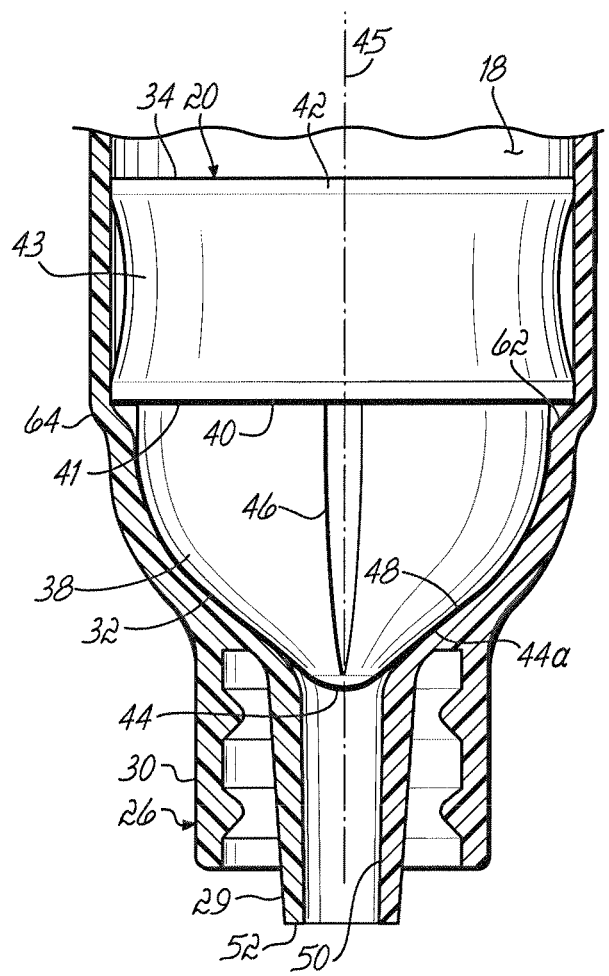
FIG. 7 is a cross-sectional view illustrating the piston of the syringe of FIG. 1 at the first end of the syringe barrel.

With reference to FIGS. 2 and 7, an exemplary piston 20 is shown. In this embodiment, the piston 20 includes a first end 32 configured to force liquid material through the first end 14 of the barrel 12 and into the dispensing tip 22. The first end 32 of the piston 20 mates with the first end 14 of the barrel 12 to force liquid material into the dispensing tip 22. The second, opposite end 34 of the piston 20 is exposed to an actuator, such as the source of pressurized air 36 (FIG. 1), whereby the piston 20 may be actuated in a direction from the second end 16 of the barrel 12 toward the first end 14 of the barrel 12. At least one first circumferential wiper 40 extends radially outwardly from a hemispherically-shaped surface 38 of the piston 20 to sealingly engage the interior walls of the barrel 12. In the embodiment shown, the wiper 40 is in the form of a flange or skirt extending circumferentially around the body of the piston 20 and forms a step 41 relative to the hemispherically-shaped surface 38. The step 41 is believed to be important to providing a minimum dead volume within the interior reservoir 18. A second wiper 42 may be provided near the second end 34 of the piston 20, and may be formed generally the same as the first wiper 40 to sealingly engage the interior surface of the barrel 12.

The surface of the piston 20, at least proximate the first and second wipers 40, 42, and optionally in the region 43 between the first and second wipers 40, 42, may be configured to facilitate micro-venting of gaseous material, such as air that may be trapped within the interior reservoir 18, while preventing liquid material from escaping the interior reservoir 18. For example, the first wiper 40, the second wiper 42, and/or the region 43 may be textured in such a way that gaseous material may pass from the interior reservoir 18, but liquid material is retained in the interior reservoir 18. Alternatively, some or all of the piston 20 may be formed from material that is permeable to gases, but impermeable to liquids to facilitate passing gaseous materials from the internal reservoir 18. It will be appreciated that various other methods may be used to facilitate passing gaseous material from the internal reservoir 18, while preventing liquid material from escaping. The region 43 may also have a concave profile to minimize material shear and pressure, and to minimize entrapping gas between the first and second wipers 42, 43.

With continued reference to FIGS. 2 and 7, the first end 32 of the piston 20 has a smooth radial profile defining a generally hemispherically-shaped surface 38 that more evenly distributes pressure throughout the liquid material as the piston 20 is moved toward the first end 14 of the barrel 12 to dispense liquid material from the tip 22, and minimizes shear in the liquid material. In the embodiment shown, an apex 44 of the piston 20 forms a tip at the first end 32 of the piston 20. The apex 44 can be elongated along a central axis 45 of the piston 20 such that the apex 44 extends outwardly from the hemispherical surface 38 and can thereby extend downwardly into a portion of the male luer 26 when the piston 20 is engaged with the second end 14 of the barrel 12. The elongated apex 44 includes a curved region 44a that provides a smooth transition from the hemispherically-shaped surface 38 and forms a bullet-nose shape, for example. This elongated apex 44 of the piston 20 helps to dispense liquid material through the dispensing tip 22 and minimizes waste retained within the dispenser 10.

The piston 20 may further include flow passages 46 defined on the hemispherically-shaped surface 38 of the piston 20, between the apex 44 and the first wiper 40. The flow passages 46 may be defined by channels formed into the outer surface 38 of the piston 20, or they may be defined by outwardly extending ribs or surfaces (not shown) disposed on the first end 32 of the piston 20. In the embodiment shown, the flow passages 46 are channels formed into the first end 32 of the piston 20 and are approximately 0.003 to 0.005 inch deep.

When the barrel reservoir 18 is filled from the first end 14 of the barrel 12, liquid material is directed along the flow passages 46 from the apex 44 of the piston 20 toward the first wiper 40. The movement of liquid material along flow passages 46 forces entrapped air toward the first wiper 40 where the air may pass through. The wiper 40, however, prevents the liquid material from material from passing. In this way, the accumulation of air beneath the first wiper 40 is reduced or eliminated.

In the embodiments illustrated in FIGS. 3A-3B, the first end 14 of the syringe barrel 12 and a dispensing tip 22 are shown in more detail. The barrel 12 cooperates with the design of the dispensing tip 22 to minimize the shear of liquid material and to reduce or eliminate the formation of air pockets within the barrel reservoir 18 during filling and/or dispensing operations. To this end, the first end 14 of the barrel 12 includes a smoothly curved profile 48 corresponding to the hemispherically-shaped surface 38 of the first end 32 of the piston 20. In one embodiment, the curved profile 48 may include a radius in the range of about 5/32-inch to about 3/16-inch, or greater. The curved profile 48 helps to direct liquid material through an outlet passageway 50 and outlet orifice 52 at the first end 14 of the barrel 12 to provide smooth transition into the inlet 54 of the dispensing tip 22. The inner diameter of the outlet passageway 50 may be tapered to minimize shear in the liquid material as it is dispensed from the barrel 12 into the dispensing tip 22. In the embodiment depicted in FIG. 3A, the outlet orifice 52 of the syringe barrel 12 has a relatively blunt shape. Alternatively, the outlet orifice 52*a* of the barrel 12 may be flared gradually outwardly toward the interior of the dispensing tip inlet 54 to provide a smooth transition between the first end 14 of the barrel 12 and the dispensing tip 22, as depicted in FIG. 3B. The interior of the dispensing tip inlet 54 may have generally frustoconically-shaped sidewalls or "bullet-nose"-shaped sidewalls to minimize entrapment of air within the dispensing tip 22, and to provide a generally smooth transition between the inlet 54 of the dispensing tip 22 and the outlet passageway 56.

With continued reference to FIG. 3A, the outlet passageway 50 of the syringe barrel 12 extends over a circumferential groove 60 formed in the inlet 54 of the dispensing tip 22. This groove 60, or "stripper ring" is formed into the dispensing tip 22 during a molding process and helps to retain the dispensing tip 22 on one half of a removable core member as the other half of the core is removed from the molded tip 22. The tip 22 is subsequently ejected from the core member and the stripper ring 60 remains within the inlet passageway of the dispensing tip 22.

The first end 14 of the syringe barrel 12 further includes an interior ledge 62 adapted to engage the first wiper 40 on the piston 22 as the piston 22 engages the interior surface at the first end 14 of the barrel 12. As the interior ledge 62 engages the first wiper 40, liquid material beneath the wiper 40 is further forced from the wiper 40, thereby reducing liquid material waste. In the embodiment shown, the barrel 12 is provided with a uniform wall thickness such that the interior ledge 62 creates a corresponding radially outwardly extending ledge 64 on the exterior surface of the barrel 12, giving a distinctive visual appearance to the first end 14 of the syringe barrel 12.

With continued reference to FIGS. 2 and 3, the second end 16 of the syringe barrel 12 includes a terminal open end such as a relatively large diameter opening 70 and has a radially outwardly extending flange 72. A pair oppositely disposed tabs or ears 74, 76 extend radially outwardly from the flange 72, in opposite directions, to facilitate securing an end cap 110 or an adapter 80 for coupling the syringe 10 to an actuator, as will be described in more detail below. The radially extending length of the ears 74, 76 is generally smaller than conventional syringe ears to minimize flexure of the ears 74, 76 during use. This flexure can cause variations in dispensed volumes of liquid material when a pressure pulse is applied to the syringe 10 to cause the piston 20 to move in a direction toward the first end 14 of the barrel 12. Repeated flexure of the ears 74, 76 over time can fatigue the material of the barrel 12, thereby further increasing deflection of the ears 74, 76 and the variation in dispensed volumes of liquid material. Advantageously, the reduced lengths of the ears 74, 76 in the syringe 10 of the embodiment shown reduces the flexure of the ears 74, 76 thereby improving the consistency of the volumes of liquid material dispensed from the syringe 10. In the embodiment shown, each ear 74, 76 further includes a radially outwardly extending detent or bump 78, formed on an outer periphery thereof, to provide positive engagement with an end cap 110 or an adapter 80 which may be coupled to the second end 16 of the barrel 12, as described in more detail below.

Figure 6:
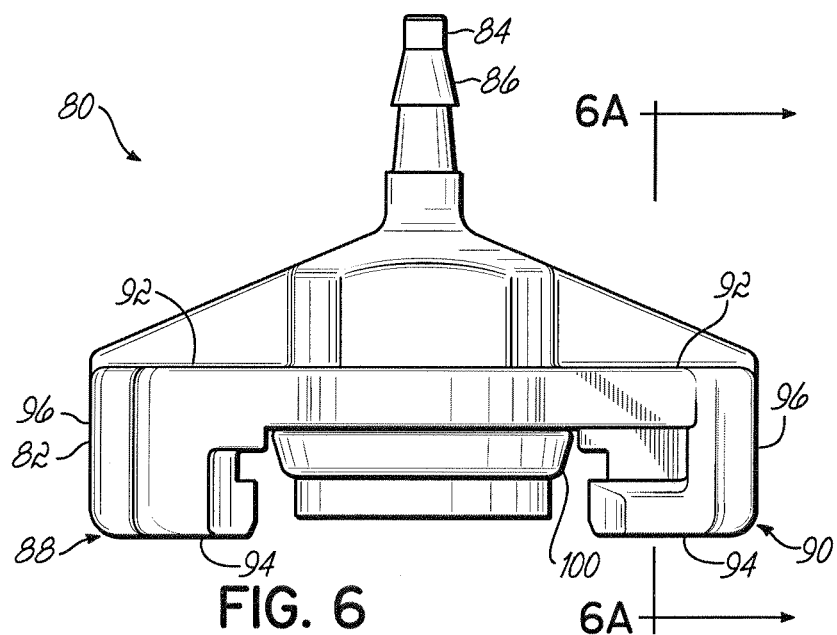
FIG. 6 is a side elevation view of an exemplary adapter, as shown in FIGS. 1-2, for use with the syringe barrel of FIG. 3.
Figure 6A:
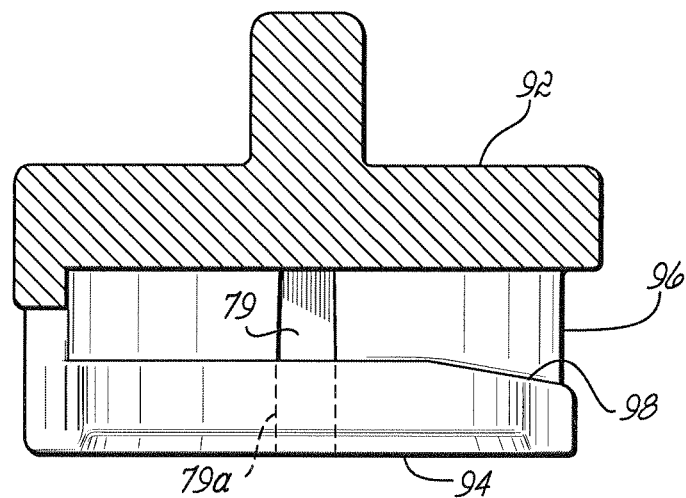
FIG. 6A is a cross-sectional view of the adapter of FIG. 6, taken along line 6A-6A.

FIGS. 6 and 6A illustrate an exemplary adapter 80 configured to be coupled to the second end 16 of the syringe barrel 12 to facilitate coupling the syringe 10 to an actuator, such as a source of pressurized air 36. In the embodiment shown, the adapter 80 includes a first end 82 adapted to be coupled to the second end 16 of the barrel 12, and a second end 84 adapted to be coupled to a conduit (not shown) which communicates with a source of pressurized air 36. The second end 84 of the adapter may include a barb 86 to facilitate securing the conduit thereto. The first end 82 of the adapter 80 includes first and second oppositely disposed hubs 88, 90 for engaging the first and second ears 74, 76 at the second end 16 of the barrel 12, in a bayonet-type fashion. Each hub 88, 90 is defined by a radially extending rim 92, an end wall 94 spaced from the rim 92, and a circumferentially extending sidewall 96 extending therebetween. The end wall 94 has an interior surface 98 (FIG. 6A) that is sloped in a direction toward the rim 92 to draw the adapter 80 tightly against the second end 16 of the barrel 12 as the adapter 80 is twisted to receive the ears 74, 76 within the respective hubs 88, 90 of the adapter.

With continued reference to FIGS. 6 and 6A, and referring to FIG. 2, the first end 82 of the adapter 80 further includes a seal 100 disposed on a protrusion such as a centrally located cylindrical boss 102 that protrudes from the end wall 94 in a direction opposite the second end 84. A radially outwardly extending flange 104 retains the seal 100 on the cylindrical boss 102. In the embodiment shown, seal 100 is an O-ring, but it will be appreciated that various other types of sealing devices may alternatively be used. When mounted to the syringe barrel 12, the seal extends axially within the second end 16 of the syringe barrel 12 to engage an interior surface of the syringe barrel 12. To fully engage the seal 100 with the interior surface of the syringe barrel 12, the adapter 80 must be rotated to receive the ears 74, 76 of the syringe barrel 12 within the hubs 88, 90 of the adapter 80. As the ears 74, 76 are received within the hubs 88, 90 of the adapter 80, the sloped surface 98 of the end wall 94 draws the seal 100 into the second end 16 of the barrel 12 and the seal 100 sealingly engages the interior surface of the syringe barrel 12.

Prior to twisting the adapter 80 to receive the ears 74, 76 within the hubs 88, 90 of the adapter 80, air can escape from the interior of the reservoir 18 past the seal 100. When the ears 74, 76 are positioned fully within the hubs 88, 90 of the adapter 80, the detents 78 formed on the ears 74, 76 engage corresponding slots 79 (FIG. 6A) formed into the side walls 96 of the adapter 80 to provide a snap fit of the adapter 80 to the ears 74, 76 of the barrel 12, thereby providing a positive indication that the adapter 80 is fully locked onto the second end 16 of the barrel 12. In the embodiment shown, the slots 79 are formed by apertures 79*a* formed through the end walls 94 and extending into the sidewalls 96.

The seal 100 engages a chamfer 106 (FIG. 3) formed on the second end 16 of the syringe barrel and adjacent the opening 70. Location of the chamfer 106 at the opening 70 ensures that seal 100 will not extend too far into the syringe barrel 12 and thereby provides an indication of whether the adapter 80 is properly seated and locked onto the syringe barrel 12. When the adapter 80 is not properly seated and locked, the adapter 80 will easily slip off of the second end 16 of the syringe barrel 12 due to the shallow engagement of the seal 100 with chamfer 106.

Figure 4:
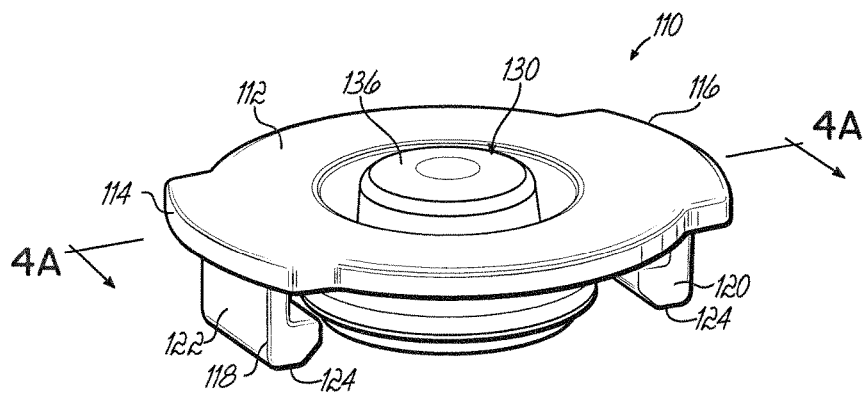
FIG. 4 is a perspective view of an exemplary end cap for use with the syringe barrel of FIG. 3.
Figure 4A:
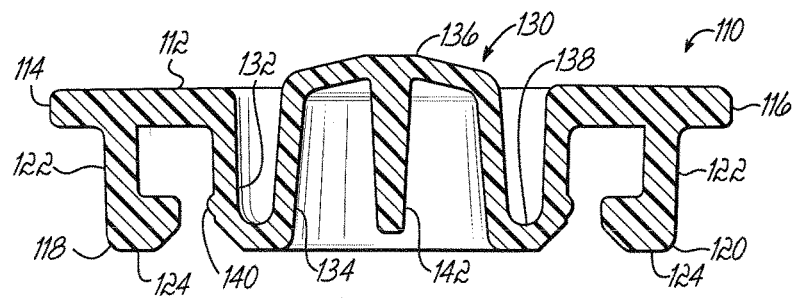
FIG. 4A is a cross-sectional view of the end cap of FIG. 4, taken along line 4A-4A.

FIGS. 4 and 4A depict a closure such as an end cap 110 that may be secured to the second end 16 of the syringe barrel 12, in place of adapter 80. The end cap 110 includes an annular brim 112 and first and second oppositely disposed flanges 114, 116 extending generally radially outwardly from the brim 112. First and second oppositely disposed engagement tabs 118, 120, similar to the hubs 88, 90 of the adapter 80, extend from a bottom side of the brim 112 for engaging the ears 74, 76 of the barrel 12. Each engagement tab 118, 120 comprises a sidewall 122 extending perpendicular to the brim 112, and an end wall 124 extending parallel to the brim 112. The end wall 124, brim 112, and sidewall 122 thereby define generally circumferentially extending slots adapted to receive the first and second ears 74, 76 provided on the second end 16 of the syringe barrel 12.

The end cap 110 further comprises a generally hat-shaped central portion 130 defined by first and second concentric sidewalls 132, 134 and an end wall 136. The first sidewall 132 extends axially from the brim 112 and is joined to the second sidewall 134 by an arcuate end portion 138 extending therebetween. The end wall 136 is provided on the second end of the second sidewall 134 and closes the cap. The central portion 130 of the end cap 110 permits the brim 112 to flex, thereby facilitating closure of the second end 14 of the syringe barrel 12 with the end cap 110. A generally circumferentially extending sealing bead 140 is disposed on the first sidewall 132 of the central portion 130 to provide sealing engagement of the end cap 110 with an interior surface of the syringe barrel 12. An elongate stem 142 is centrally located on the end wall 136 and extends downwardly from the end wall 136. Stem 142 facilitates the formation of the end wall 136 during manufacture. To seal the second end 14 of the barrel 12 with the end cap 110, the first tab 118 is engaged with the first ear 74 at the second end 14 of the barrel 12, and the second tab 120 is pivoted downwardly to snap over the second ear 76 while compressing the central portion 130 to cause the second tab 120 to flexibly extend over the second ear 76.

Figure 5:
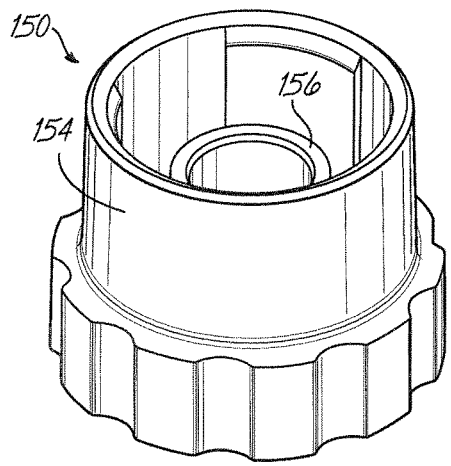
FIG. 5 is a perspective view of an exemplary tip cap for use with the syringe barrel of FIG. 3.
Figure 5A:
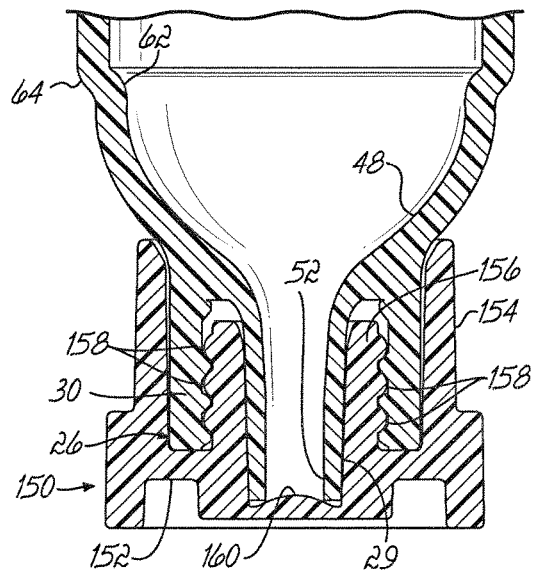
FIG. 5A is a cross-sectional view illustrating the tip cap of FIG. 5 on the syringe barrel of FIG. 3.

FIGS. 5 and 5A depict an exemplary tip cap 150 that may be used with the syringe 10. The tip cap 150 is configured to fit over the male luer 26 at the first end 14 of the syringe barrel 12. In the embodiment shown, the tip cap 150 includes a generally circular end wall 152, although it will be appreciated that the end wall 152 may have various other shapes. The end wall 152 may have flutes, lobes, or other features disposed around its outer periphery to facilitate gripping the tip cap 150 during installation or removal of the tip cap 150 from the syringe barrel 12. A generally cylindrical skirt 154 extends from the end wall 152 and is sized to be received over the collar 30 of the male luer 26. A generally cylindrical boot 156 also extends from the end wall 152 and is located concentrically within the skirt 154 to be received between the male connecting tip 29 and the collar 30 of the male luer 26. The skirt 154 and boot 156 are sized and dimensioned to provide a frictional fit on the male luer 26 such that the tip cap 150 is retained on the first end 14 of the syringe barrel 12. When the tip cap 150 is firmly seated on the male luer 26 of syringe barrel 12, a raised, central bead 160 disposed on an interior side of the end wall 152 sealingly engages the outlet orifice 52 at the first end 14 of the syringe barrel 12.

The tip cap may 150 further include one or more circumferentially extending ribs or ridges 158 provided on the boot 156 and sized to engage the threads of the male luer 26. The ribs 158 may be configured such that the tip cap 150 can be pressed axially onto the first end 14 of the syringe barrel 12, whereby the boot 156 deforms radially inwardly so that the ribs 158 ride over the threads 31 on the male luer 26. Alternatively, the tip cap 150 may be placed onto the first end 14 of the syringe barrel 12 by twisting the tip cap 150 to advance the tip cap 150 over the threads of the male luer 26. The tip cap 150 may be removed from the first end 14 of the syringe barrel 12 by twisting the tip cap 150.

While the present invention has been illustrated by the description of various exemplary embodiments thereof, and while the embodiments have been described in considerable detail, they are not intended to restrict or in any way limit the scope of the appended claims to such detail. The various features discussed herein may be utilized alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. An adapter for coupling a syringe dispenser to a source of pressurized fluid, the adapter comprising:
   a first end adapted to be coupled to a syringe barrel having a terminal open end and oppositely disposed ears proximate to the open end for engaging the adapter;
   a second end adapted to be coupled to a source of pressurized fluid;
   first and second hubs on said first end of said adapter for engaging the ears on the barrel, each hub comprising a radially extending rim, an end wall spaced from said rim, and a circumferentially extending sidewall extending between said rim and said end wall;
   a seal fixedly mounted on a protrusion extending from said rim and configured to engage the terminal open end of the barrel, said seal sealingly engaging the terminal open end of the barrel when said first and second hubs are manipulated to engage the ears on the barrel; and
   a slot disposed in at least one side wall of said first and second hubs, said slot positioned to engage a corresponding detent on at least one ear of the barrel when said first and second hubs are manipulated to engage the ears on the barrel such that the at least one ear is restricted from moving relative to the first and second hubs, said slot formed by an aperture formed through at least one end wall of said first and second hubs and extending into the at least one side wall of said first and second hubs,
   wherein said end wall of each hub of the first and second hubs includes a radially sloped surface, said radially sloped surface extending circumferentially along a portion of said end wall, said radially sloped surface drawing said seal into sealing engagement with the open end of the barrel when said first and second hubs are manipulated to engage the ears on the barrel.

2. The adapter of claim 1, wherein said seal comprises an O-ring positioned to engage an interior surface of the barrel when said first and second hubs are manipulated to engage the ears on the barrel.

3. A dispensing syringe, comprising:
   a syringe barrel, said syringe barrel comprising:
      an elongate tubular body including at least one sidewall and having a first end, a second end, an interior reservoir, and oppositely disposed ears proximate said second end,
      said sidewall defining a hemispherically-shaped portion within said interior reservoir proximate said first end of said body, and a piston within said interior reservoir, said piston comprising:
a piston body having a first end and a second end,
said first end having a hemispherically-shaped surface about an axis of revolution, and an apex extending outwardly from said hemispherically-shaped surface along said axis of revolution, said hemispherically-shaped surface of said piston being complementary to said hemispherically-shaped portion of said syringe barrel; and
an end cap coupled to said second end of said syringe barrel, the end cap comprising:
an annular brim;
first and second engagement tabs provided on oppositely disposed sides of said brim;
each of said first and second engagement tabs including a sidewall and an end wall that cooperate with said brim to define a space adapted to receive one of the ears of the barrel in the space between said brim, said sidewall, and said end wall; and
a flexible central portion configured to be disposed radially interiorly of said brim, said flexible central portion flexurally deformable to facilitate snap-fit installation of said engagement tabs around the ears of the barrel, such that the ears are received in said space defined by said sidewalls and said end walls of said first and second engagement tabs and said brim,
said flexible central portion including an end wall that closes off the open end of the syringe barrel when then end cap is secured to the syringe dispenser,
said flexible central portion comprising first and second concentric sidewalls joined together by an arcuate end portion.

4. A syringe, comprising:
an elongate tubular body including at least one sidewall and having a first end, a second end, and an interior reservoir; and
a piston disposed at least partly within the interior reservoir,
said at least one sidewall defining a hemispherically-shaped portion within said interior reservoir proximate to said first end of said body; and
a radially inwardly extending ledge within said interior reservoir configured to contact said hemispherically-shaped portion, said sidewall having a uniform thickness proximate said ledge, whereby the location of said radially inwardly extending ledge is visible externally of said body by a corresponding radially outwardly extending ledge,
said ledge configured to engage a wiper seal on a hemispherically-shaped portion of the piston when the hemispherically-shaped portion of the piston engages the hemispherically-shaped portion of the sidewall,
said wiper seal comprising a radially outwardly flared skirt,
said ledge configured to displace liquid material beneath the wiper seal when the ledge engages with the wiper seal.

5. A dispensing syringe, comprising:
a syringe barrel, said syringe barrel comprising:
an elongate tubular body including at least one sidewall and having a first end, a second end, an interior reservoir, and oppositely disposed ears proximate said second end,
said sidewall defining a hemispherically-shaped portion within said interior reservoir proximate said first end of said body, and
a radially inwardly extending ledge within said interior reservoir adjacent said hemispherically-shaped portion, said sidewall having a uniform thickness proximate said ledge, whereby said ledge is visible externally of said body;
a piston within said interior reservoir, said piston comprising:
a piston body having a first end and a second end,
said first end having a hemispherically-shaped surface about an axis of revolution, and an apex extending outwardly from said hemispherically-shaped surface along said axis of revolution, said hemispherically-shaped surface of said piston being complementary to said hemispherically-shaped portion of said syringe barrel; and
an end cap coupled to said second end of said syringe barrel, said end cap comprising:
an annular brim,
first and second engagement tabs provided on oppositely disposed sides of said brim, and
a flexible central portion configured to be disposed radially interiorly of said brim, said flexible central portion flexurally deformable to facilitate snap-fit installation of said engagement tabs over said ears of said tubular body of said syringe barrel.

6. The dispensing syringe of claim 5, wherein said piston is configured to permit gas to pass from said volume while retaining liquid within said volume.

7. The dispensing syringe of claim 5, wherein said apex of said hemispherically-shaped surface has a bullet-nose-shape.

8. The dispensing syringe of claim 5, wherein each ear of said first and second oppositely disposed ears has a radial extent that is smaller than a circumferential length of said ear, whereby said first and second oppositely disposed ears resist flexural bending during use of the dispensing syringe to dispense a liquid material therefrom.

9. The dispensing syringe of claim 8, further comprising:
at least one detent on at least one of said first and second oppositely disposed ears for providing secure engagement with a closure attached to said second end of said barrel.

10. The dispensing syringe of claim 5, further comprising:
a luer connector disposed at said first end of said barrel; and
said luer connector defining an outlet orifice and an outlet passage in fluid communication between said outlet orifice and said interior reservoir,
said outlet passage being tapered along an axial length thereof.

11. The dispensing syringe of claim 10, further comprising a radially outwardly flared portion proximate to said outlet orifice to provide a smooth transition of fluid flow between said interior reservoir and said outlet orifice.

12. The dispensing syringe of claim 5, wherein said first end of said syringe barrel includes a male luer connector with an outlet orifice, the dispensing syringe further comprising:
a tip cap coupled to said first end of said syringe barrel, said tip cap comprising:
an end wall;
a skirt extending from said end wall;

an annular boot extending from said end wall and concentrically positioned within said skirt, said boot spaced from said skirt to define a space for frictionally gripping said male luer connector therein;

at least one circumferential rib on said boot and sized to engage corresponding threads on said male luer connector of said syringe barrel; and a central bead on said end wall, said central bead sealingly engaging said outlet orifice of said male luer connector when said tip cap is firmly seated on said male luer connector.

13. A dispensing syringe, comprising:

a syringe barrel, said syringe barrel comprising:

an elongate tubular body including at least one sidewall and having a first end, a second end, an interior reservoir, and oppositely disposed ears proximate said second end, said sidewall defining a hemispherically-shaped portion within said interior reservoir proximate said first end of said body, and a radially inwardly extending ledge within said interior reservoir adjacent said hemispherically-shaped portion, said sidewall having a uniform thickness proximate said ledge, whereby said ledge is visible externally of said body;

a piston within said interior reservoir, said piston comprising:

a piston body having a first end and a second end, said first end having a hemispherically-shaped surface about an axis of revolution, and an apex extending outwardly from said hemispherically-shaped surface along said axis of revolution, said hemispherically-shaped surface of said piston being complementary to said hemispherically-shaped portion of said syringe barrel; and an adapter coupled to said second end of said syringe barrel, said adapter comprising:

a first end adapted to be coupled to said second end of said syringe barrel a second end adapted to be coupled to a source of pressurized fluid;

first and second hubs on said first end of said adapter for engaging the ears on the barrel, each hub comprising a radially extending rim, an end wall spaced from said rim, and a circumferentially extending sidewall extending between said rim and said end wall;

a seal fixedly mounted on a protrusion extending from said rim and configured to engage the terminal open end of the barrel, said seal sealingly engaging the terminal open end of the barrel when said first and second hubs are manipulated to engage the ears on the barrel; and a slot disposed in at least one side wall of said first and second hubs, said slot positioned to engage a corresponding detent on at least one ear of the barrel when said first and second hubs are manipulated to engage the ears on the barrel such that the at least one ear is restricted from moving relative to the barrel, said slot formed by an aperture formed through at least one end wall of said first and second hubs and extending into the at least one side wall of said first and second hubs.

14. The dispensing syringe of claim 13, wherein said end wall of each hub of the first and second hubs includes a radially sloped surface, said radially sloped surface extending circumferentially along a portion of said end wall, said radially sloped surface drawing said seal into sealing engagement with the open end of the barrel when said first and second hubs are manipulated to engage the ears on the barrel.

15. The dispensing syringe of claim 13, further comprising:

a luer connector at said first end of said elongate tubular body, said luer connector adapted for receiving a dispensing tip, said luer connector including:

a tubular wall defining an outlet orifice and an outlet passage in fluid communication between said outlet orifice and said interior reservoir, and a collar disposed outside the tubular wall along a radial direction and surrounding a portion of the tubular wall about a circumferential direction, the collar including internal threads on an internal surface of the collar, a distal end of the tubular wall extending beyond a distal end of the collar along a longitudinal direction that is perpendicular to the radial direction, said outlet passage being tapered along an axial length thereof.

* * * * *